US007797810B2

(12) United States Patent
Hermansson

(10) Patent No.: US 7,797,810 B2
(45) Date of Patent: *Sep. 21, 2010

(54) METHOD OF MANUFACTURING ABSORBENT ARTICLE

(75) Inventor: Kent Hermansson, Västra Frölunda (SE)

(73) Assignee: SCA Hygiene Products AB, Gothenburg (SE)

(*) Notice: Subject to any disclaimer, the term of this patent is extended or adjusted under 35 U.S.C. 154(b) by 13 days.

This patent is subject to a terminal disclaimer.

(21) Appl. No.: 12/314,183

(22) Filed: Dec. 5, 2008

(65) Prior Publication Data

US 2009/0083961 A1 Apr. 2, 2009

Related U.S. Application Data

(62) Division of application No. 10/321,483, filed on Dec. 18, 2002, now Pat. No. 7,481,802.

(60) Provisional application No. 60/342,760, filed on Dec. 28, 2001.

(51) Int. Cl.
*B23P 21/00* (2006.01)
*A61F 13/15* (2006.01)
(52) U.S. Cl. .......................... 29/469; 604/396
(58) Field of Classification Search .............. 29/428, 29/469; 604/358–402; 2/400–408; 524/1; 156/259, 258, 229; 442/370
See application file for complete search history.

(56) References Cited

U.S. PATENT DOCUMENTS

| 2,012,879 A | 8/1935 | Kneibler |
| 3,794,034 A | 2/1974 | Jones, Sr. |
| 3,912,565 A | 10/1975 | Koch et al. |
| 4,023,216 A | 5/1977 | Li |
| 4,037,602 A | 7/1977 | Hawthorne |
| 4,675,012 A | 6/1987 | Rooyakkers |
| 4,729,131 A | 3/1988 | Thygesen |
| 4,808,252 A | 2/1989 | Lash |
| 4,838,886 A | 6/1989 | Kent |
| 4,938,757 A | 7/1990 | Van Gompel et al. |
| 5,156,902 A | 10/1992 | Pieper et al. |
| 5,290,270 A | 3/1994 | Fisher |

(Continued)

FOREIGN PATENT DOCUMENTS

EP 0 157 649 10/1985

(Continued)

OTHER PUBLICATIONS

U.S. Appl. No. 10/179,273; Cecile Sanlin et al., filed Jun. 26, 2002.

(Continued)

*Primary Examiner*—John C Hong
(74) *Attorney, Agent, or Firm*—Buchanan Ingersoll & Rooney PC

(57) ABSTRACT

An absorbent article of pants shape including an elastic waist portion, an absorbent element (5), and a liquid-impermeable outer layer (3) which is intended to enclose the absorbent element on at least that side thereof which faces away from the wearer during use of the article. Elastic members are arranged along the edges of a second piece, along at least the crotch portion for the forming of leg elastics.

11 Claims, 5 Drawing Sheets

U.S. PATENT DOCUMENTS

| | | |
|---|---|---|
| 5,291,617 A | 3/1994 | Moretz |
| 5,401,266 A | 3/1995 | Runeman et al. |
| H1440 H | 5/1995 | New et al. |
| 5,486,168 A | 1/1996 | Runeman et al. |
| 5,554,145 A | 9/1996 | Roe et al. |
| 5,558,734 A | 9/1996 | Sherrod et al. |
| 5,628,737 A | 5/1997 | Dobrin et al. |
| 5,749,866 A | 5/1998 | Roe et al. |
| 5,785,699 A | 7/1998 | Schmitz |
| 5,810,799 A | 9/1998 | Slater |
| 5,957,908 A | 9/1999 | Kline et al. |
| 6,023,789 A | 2/2000 | Wilson et al. |
| 6,086,571 A | 7/2000 | Guevara et al. |
| 6,241,716 B1 | 6/2001 | Ronnberg |
| 6,352,607 B1 | 3/2002 | Kuen et al. |
| 6,508,799 B1 | 1/2003 | Freiburger et al. |
| 6,569,141 B1 | 5/2003 | Bruemmer-Prestley et al. |
| D492,090 S | 6/2004 | Oya et al. |
| 7,172,585 B2 * | 2/2007 | Sandin et al. ............ 604/385.3 |
| 7,662,138 B2 * | 2/2010 | Hermansson et al. ....... 604/396 |
| 2001/0000529 A1 | 4/2001 | Ronnberg |
| 2001/0041879 A1 | 11/2001 | Karami et al. |
| 2002/0138065 A1 | 9/2002 | Yeater |
| 2002/0151864 A1 | 10/2002 | Otsubo et al. |
| 2003/0181883 A1 | 9/2003 | Olson et al. |

FOREIGN PATENT DOCUMENTS

| | | |
|---|---|---|
| EP | 0 196 654 A2 | 10/1986 |
| EP | 0 196 654 B1 | 10/1986 |
| EP | 0 238 200 A2 | 9/1987 |
| EP | 0 225 909 | 11/1989 |
| EP | 0 388 372 A1 | 9/1990 |
| EP | 0 525 778 A2 | 7/1992 |
| EP | 0 560 630 A1 | 9/1993 |
| EP | 0 878 180 | 11/1998 |
| EP | 1 050 288 A2 | 11/2000 |
| EP | 1 078 620 A2 | 2/2001 |
| EP | 1077054 A2 | 2/2001 |
| GB | 2 112 267 A | 7/1983 |
| GB | 2264258 A | 8/1993 |
| JP | 61-000602 | 1/1986 |
| JP | 62-050616 U | 3/1987 |
| JP | 01-107319 U | 7/1989 |
| JP | 03-195555 | 8/1991 |
| JP | 05-009530 U | 2/1993 |
| JP | 05-501976 T | 4/1993 |
| JP | 07-047097 | 2/1995 |
| JP | 10-512174 T | 11/1998 |
| JP | 10-317207 | 12/1998 |
| JP | 2000-300603 A | 10/2000 |
| JP | 2000-342621 | 12/2000 |
| JP | 2000-342621 A | 12/2000 |
| SE | 9904202-0 | 11/1988 |
| WO | WO 91/07156 | 5/1991 |
| WO | WO 96/05786 | 2/1996 |
| WO | WO 96/32083 | 10/1996 |
| WO | WO 99/42066 | 8/1999 |
| WO | WO 00/61049 | 10/2000 |
| WO | WO 01/13843 | 3/2001 |
| WO | WO 01/13851 A1 | 3/2001 |
| WO | WO 01/15898 A1 | 3/2001 |
| WO | WO 01/35890 | 5/2001 |

OTHER PUBLICATIONS

U.S. Appl. No. 10/321,487; Kent Hermansson, filed Dec. 18, 2002.
U.S. Appl. No. 10/321,569; Kent Hermansson, filed Dec. 18, 2002.
Notice of Reason for Rejection in JP 2003-559391 dated May 27, 2008.

* cited by examiner

METHOD OF MANUFACTURING ABSORBENT ARTICLE

CROSS-REFERENCE TO RELATED APPLICATIONS

The present application is a divisional of U.S. application Ser. No. 10/321,483, filed in the United States on Dec. 18, 2002, now U.S. Pat. No. 7,481,802 wherein U.S. application Ser. No. 10/321,483 claims the benefit of U.S. Provisional Application No. 60/342,760, filed in the United States on Dec. 28, 2001, the entire contents of which are hereby incorporated herein by reference.

BACKGROUND OF THE APPLICATION

1. Technical Field

The present invention relates to an absorbent article of pants-like shape, such as incontinence pants, pants diapers or sanitary towel pants, comprising an elastic waist portion, an absorbent element, which has a length and a width and is intended to at least cover the genitals of the wearer during use of the article. The invention also relates to a method of manufacturing such absorbent articles of pants-like shape.

2. Background Art

Absorbent disposable products for taking up urine, feces or menstrual blood have developed greatly since they came into more general use during the 1960s and 1970s. As they are disposable products, it is necessary that they can be manufactured and sold at a very low price. At the same time, it is important that the products function well and reliably. Good fit and comfort are also important characteristics. The first disposable diapers were made of two-part products, consisting of an outer pant made of plastic, intended to be re-used, and a rectangular absorbent insert for disposable use. The absorbent material in these inserts initially consisted of cellulose tissue. Later, better absorption materials made of what is known as fluff pulp made of cellulose were developed. The fit and comfort of these early diapers were poor. The products were unwieldy and uncomfortable for the wearer. Towards the end of the 1970s, the first complete disposable diapers arrived, that is to say diapers in which the absorption bodies were integrated with a liquid-impermeable outer layer. The absorption materials have developed and improved, which has resulted in the possibility of the absorption bodies being adapted better to the anatomy of the wearer. Hourglass-shaped absorption bodies with a narrower crotch portion between the two end portions are now predominant. The trend has also been towards increasingly thin products, which has been made possible by the inclusion of what are known as superabsorbent materials in the absorption body. There are many reasons why thinner and even smaller absorption bodies are desirable. A thinner, smaller absorption body is more comfortable and more discreet, which is especially important for adult incontinent wearers. A reduction in volume is also very important financially because the product then requires less storage space and is easier to transport and takes up less shelf space in shops. This is important for the financial management of the shops, and if a manufacturer can produce products requiring less space in the shops than the products of the competitors, this affords a not inconsiderable competitive advantage. Moreover, there is increased pressure from authorities, in particular as far as disposable articles are concerned, to use as little material as possible for the purpose of reducing the burden on the environment.

The smaller the absorption bodies become, the more important it becomes that the absorption bodies come to lie in the correct place directly in front of the genitals of the wearer and remain in place during use even when the wearer is very active and moves a great deal. The demands of consumers for discretion, comfort and reliable functioning are also increasingly exacting. Requirements for the absorption body to come to lie correctly when put on and then be retained in the correct place have therefore increased the need for good fixing of the article on the body and the need for very good adaptability to the body when the wearer moves, at the same time as requirements have increased for the article always to come to lie in the correct place when the article is put on the wearer. This has led to the development of what are known as pants diapers, which have elastic portions for improved fit and comfort and increased flexibility during movements of the wearer compared with conventional absorbent articles.

An early patent publication relating to pants diapers of the disposable type is GB 2 112 267-A. However, this publication from 1983 discloses primitive pants diapers which did not become a commercial product. Not until the 1990s did absorbent articles of pants-like shape and construction become a major commercial product. Pants-like articles now exist in the form of diapers for infants and diapers for adults and to some extent sanitary towel pants for absorption of menstrual fluid. Previously commercially available pants diapers have been designed in principle like conventional diapers with a front portion and a rear portion and also an intermediate crotch portion, the front and rear portions being interconnected by a side seam between each leg opening and the waist opening of the pants. The pants diapers have been produced by plane diaper-like pieces being produced in a continuous web, the individual pants diapers being formed by diaper-like blanks being folded double and provided with said side seams to form pants diapers. These side seams project laterally from the finished product and are undesirable because they project and interfere with the fit of garments worn over the top. On account of their shape, they are visible through garments worn on top of the pants diapers and fitting closely around the body. They can also snag in clothing and even cause tears in nylon tights. Such projecting side seams can also chafe and give rise to pressure sores on wearers who spend a lot of time lying on their side.

WO 00/61049 has proposed improved pants diapers, in which the projecting sides seams have been eliminated. In this construction, the side seams have been eliminated by virtue of elastic side portions extending continuously in one piece from the front portion of the pants diapers to their rear portion on both sides of the pants diapers. However, the pants diapers according to WO 00/61049 have a number of disadvantages. The pants diapers according to said publication have what is referred to as a chassis, which extends over the entire pants diapers and forms the front portion, the crotch portion and the rear portion and is most reminiscent of a conventional diaper, and also said elastic side panels which each overlap the chassis at both the front and the rear on the pants diapers. These overlapping portions do not serve any actual purpose on the finished product and are in fact undesirable because a lot of material is wasted, that is to say they are used for no other purpose than joining together. The overlapping, joined-together portions are less of a nuisance and less uncomfortable for the wearer than the projecting side seams on previously known pants diapers. Owing to their unfavorable positioning, particularly at the rear, the overlapping portions can still give rise to a risk of chafing and back sores on wearers who spend a lot of time lying on their back. Another disadvantage of the pants diapers according to WO 00/61049 is that said chassis is relatively large and, as this portion is relatively rigid at least in comparison with the elastic side portions of the pants diapers, the pants diapers as a whole are not as adaptable to the body of the wearer but there is a risk that the pants diapers will be displaced from their optimum position in relation to the body when a wearer lies in bed and moves. In particular the rigid rear portion of the pants diapers can be displaced and pull both the crotch portion and the front portion from their optimum positions directly in front of the genitals of the wearer because the front and rear portion are essentially rigidly joined together in one piece with the crotch portion.

This in combination with all the above-mentioned problems associated with absorbent articles of pants-like shape has resulted in a great need to find a pants-like article which functions well in all respects and which, in addition, it is possible to manufacture rationally.

SUMMARY

According to one embodiment of the present invention, an absorbent article of pants shape comprises an elastic waist portion, an absorbent element, which has a length and a width and is adapted to at least cover the genitals of a wearer when the article is worn, and a liquid-impermeable outer layer which is adapted to enclose the absorbent element on at least a side thereof which faces away from the wearer when the article is worn, the elastic waist portion is made from an elastic first piece which is elongate in an extended state and is adapted to partly surround the trunk of the wearer when the article is worn and to form a rear portion and side portions of the absorbent article, a second piece forms a front portion and a crotch portion of the absorbent article, said second piece is elongate with two opposite end edges and two opposite longitudinal edges, the width of the second piece is, at least in the crotch portion, smaller than a length of the first piece, the second piece is arranged with its longitudinal direction at right angles in relation to a longitudinal direction of the first piece and is connected by a first end portion of the second piece to one longitudinal edge portion of the first piece centrally thereon, one end portion of the first piece is connected to a first longitudinal edge of the second piece, and another end portion of the first piece is connected in a corresponding manner to a second longitudinal edge of the second piece, the absorbent element is in its entirety arranged on the second piece, and elastic members are arranged along the longitudinal edges of the second piece along at least the crotch portion for forming leg elastics that are adapted to lie in sealing contact with legs of the wearer.

According to another embodiment, an absorbent article comprises an elastically stretchable first piece having first and second longitudinal edges and first and second ends, wherein the first and second ends are shorter than the first and second longitudinal edges; a second piece having first and second longitudinal edges and first and second ends, wherein the first and second ends are shorter than the first and second longitudinal edges; the second piece includes an absorbent element; the first end of the second piece is secured to a middle portion of the second longitudinal edge of the first piece so that the first piece extends substantially perpendicular to the second piece; the first end of the first piece is secured to the first longitudinal edge of the second piece and the second end of the first piece is secured to the second longitudinal edge of the second piece; and elastic members are arranged along at least a portion of the first longitudinal edge and along at least a portion of the second longitudinal edge of the second piece adjacent the absorbent element to contract said portions of the second piece.

By virtue of the fact that the entire rear portion of a preferred embodiment is elastic and, together with the elastic side portions, forms a single continuous elastic unity, the pants as a whole are more adaptable to body movements. Local irregularities are taken up and smoothed out by the continuous elastic piece and are not transferred to the more rigid parts of the front portion and crotch portion located directly in front of the genitals of the wearer. Compared with conventional diapers and previously known absorbent articles of pants-like shape, the embodiments of the present invention afford superior fit and comfort. Most of the pants-like garment is completely smooth. The seams required are arranged at the transition between the front portion and the first piece and at the transition between the first and the second piece in the crotch portion. These seams come to lie in places which are not subjected to any significant pressure during use of the article, and there is less risk of chafing and pressure sores caused by seams on the pants-like article. Due to the arranging of leg elastics, the article obtains a good fit and sealing around the legs of the wearer.

The embodiment is designed in only two part pieces, where the absorbent element is in its entirety located on the second part piece, which affords greater freedom of choice with regard to manufacturing method compared with previously known articles of pants-like shape.

According to one embodiment, the length of the second piece is greater than the width of the first piece, and a projecting portion of the second piece formed by the length difference is in its entirety located below that side edge of the first piece which is the lower one during use of the article, and there forms the crotch portion. According to a modified embodiment, the projecting portion has a smaller width than the remainder of the second piece.

According to another embodiment, the absorbent element extends in its longitudinal direction over the entire crotch portion and a little way up over the front portion in the direction of that side edge of the first piece which is the upper one during use of the article.

According to another embodiment, the absorbent element is arranged so as to extend with its lower end portion only a little way over the crotch portion and over less than half the extent of said projecting portion. According to another embodiment, the absorbent element tapers in the direction of the crotch portion.

According to an embodiment in which the absorbent element extends over the crotch portion, the absorbent element forms a concave shape with its side edge portions in the crotch area.

According to one embodiment, the connected side edge portions and end portions of said first and second pieces are, before connection, arranged in an overlapping manner, with the inside of an overlapping portion being arranged against the outside of an overlapped portion.

According to another embodiment, the second piece includes a liquid-permeable inner layer and said liquid-impermeable outer layer, and the absorbent element is arranged between said inner and outer layers, the inner and outer layers extending in the lateral direction and longitudinal direction outside the absorbent element and being interconnected there.

According to one embodiment, the liquid-impermeable layer only covers the absorbent element. According to one embodiment, the rest of the second piece is breathable and vapor-permeable.

According to a modified embodiment, the liquid-impermeable outer layer is breathable and vapor-permeable, and the rest of the article, over its entire area, is breathable and vapor-permeable.

According to a further embodiment, the first piece is rectangular, which simplifies the manufacturing.

According to one embodiment, the second piece has a concave portion between the first piece and up to said side edge portions of the second piece, wherein the concave portion forms cut-outs for the legs of the wearer. According to one embodiment, the elastic members extend at least along the edges of the concave portion.

According to another embodiment, the second piece is, at least along a part of its length, narrowing towards the first piece, wherein the narrowing portion forms cut-outs for the legs of the wearer. According to one embodiment, the elastic members are arranged along the edges of said narrowing portion for the forming of leg elastics.

According to one embodiment, the second piece is essentially inelastic. The term inelastic here denotes that the front section, under normally occurring stresses, does not stretch.

According to one embodiment, the elastic members extend from an area in the rear portion where the elastic first piece and the second piece overlap each other and further along the crotch portion along the edges of the second piece in a direction towards the front portion, whereby the elastic members are effectively connected with the elastic first piece. In such a design, the leg elastic is connected with the waist elastic in the first piece, which gives the pants-like article a good fit.

According to a further embodiment, the absorbent element comprises superabsorbent material and is continuously narrowing in a direction towards the rear portion of the article, and the concentration of superabsorbent material increases in the same direction.

A method of manufacturing an absorbent article according to one embodiment of the invention comprises providing an elastically stretchable first piece having first and second longitudinal edges and first and second ends, wherein the first and second ends are shorter than the first and second longitudinal edges; securing a first end of a second piece of material to a middle portion of the second longitudinal edge of the first piece so that the first piece extends substantially perpendicular to the second piece, wherein the second piece has first and second longitudinal edges that are substantially perpendicular to the first end and the first end is shorter than the first and second longitudinal edges, and wherein the second piece includes an absorbent element; securing the first end of the first piece to the first longitudinal edge of the second piece and securing the second end of the first piece to the second longitudinal edge of the second piece; and providing elastic members along at least a portion of the first longitudinal edge and along at least a portion of the second longitudinal edge of the second piece adjacent the absorbent element to contract said portions of the second piece.

According to one embodiment, the absorbent element is in its entirety arranged on the second piece forming part of the article before said piece is connected to said first piece.

According to another embodiment, a method relates to manufacturing an absorbent article of pants shape, the absorbent article comprising an elastic waist portion, an absorbent element, which has a length and a width and which covers genitals of a wearer when the article is worn, and a liquid-impermeable outer layer which encloses the absorbent element on at least a side thereof which faces away from the wearer of the article. The method comprises forming said elastic waist portion from an elastic first piece which is elongate in an extended state and partly surrounds the trunk of the wearer and forms a rear portion and side portions of the pants article when the article is worn, forming a front portion of the article and a crotch portion from a second piece, said second piece is elongate with two opposite end edges and two opposite longitudinal edges, a width of the second piece is, at least in the crotch portion, smaller than a length of the first piece, the second piece is arranged with its longitudinal direction at right angles in relation to the longitudinal direction of the first piece, connecting a first end portion of the second piece to one longitudinal edge portion of the first piece, centrally thereon, connecting one end portion of the first piece to a first longitudinal edge portion of the second piece, and connecting another end portion of the first piece in a corresponding manner to a second longitudinal edge portion of the second piece, and elastic members are arranged in the crotch portion on each side of the absorbent element.

BRIEF DESCRIPTION OF DRAWINGS

The invention will be described in greater detail below with reference to illustrative embodiments shown in the accompanying drawings, in which.

DETAILED DESCRIPTION OF THE PREFERRED EMBODIMENTS

Figure 1:
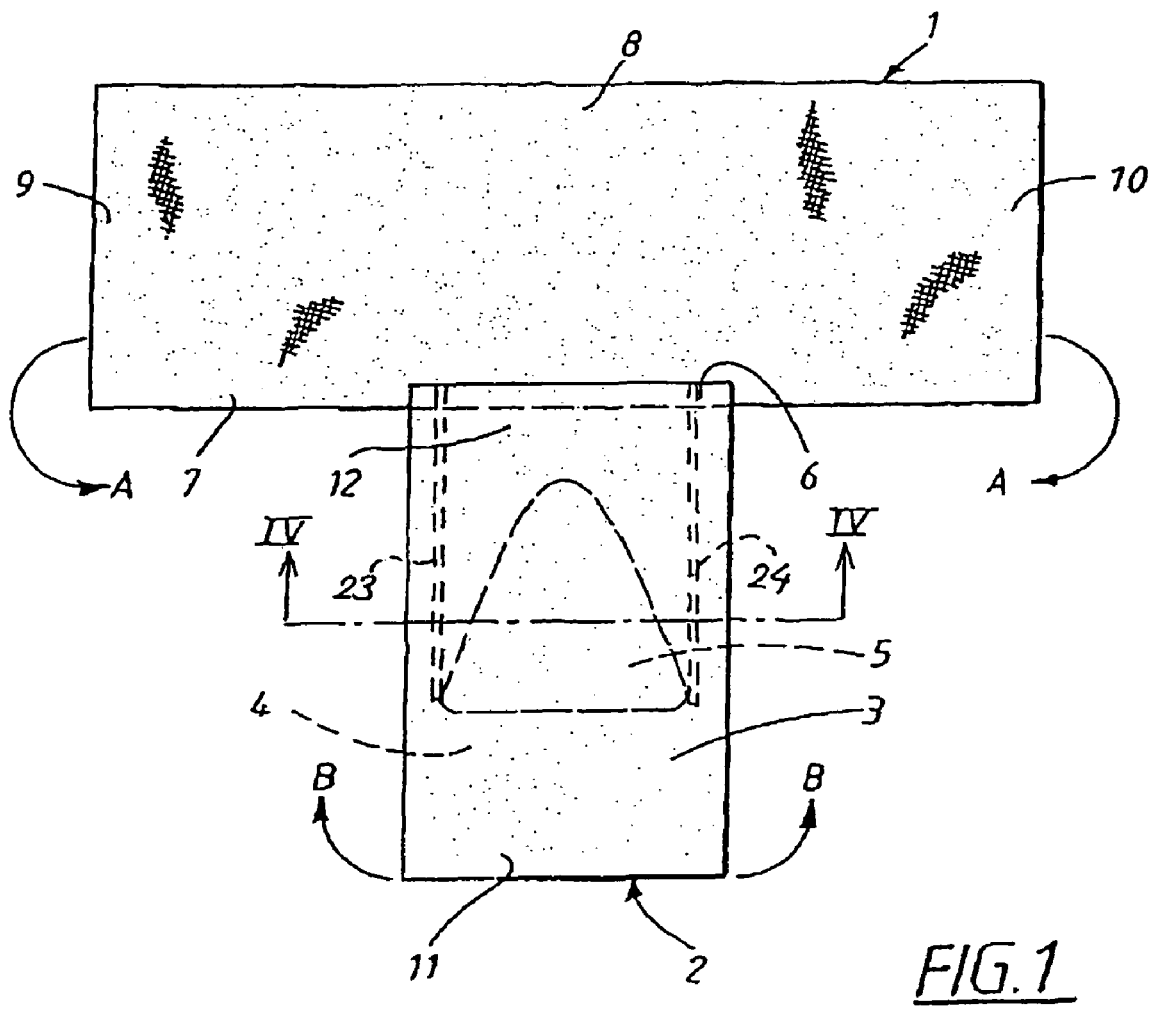
FIG. 1 shows schematically a phase of the construction of an absorbent article according to a first embodiment.

As can be seen from FIG. 1, the article in the embodiment according to FIG. 1 comprises a first piece 1. This piece is elastically stretchable and is shown in FIG. 1 in a plane and even extended state, in which the elastic piece 1 is essentially rectangular. The elastic first piece 1 can be made from conventional materials well-known to the person skilled in the art, such as woven elastic materials, elastic non-wovens, elastic laminates or elastic films. Another alternative is a material with prestressed elastic threads arranged on a supporting material, for example non-woven. Thus, the elastic piece is stretchable for a wearer when the article is put on, and it fits closely with suitable tightness around the wearer during use of the article. The tightness is of course regulated by means of size and elastic stretchability.

Figure 4:
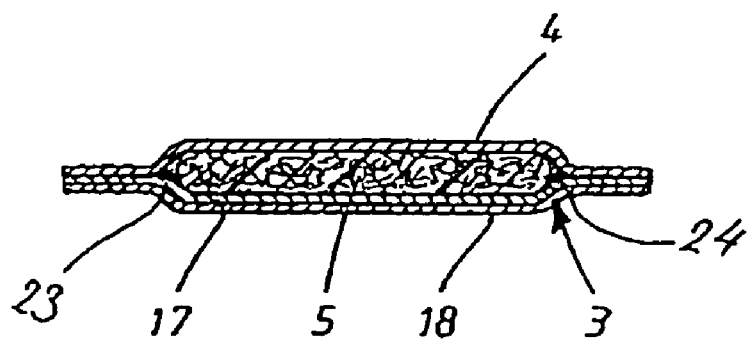
FIG. 4 shows a section along the line IV-IV in FIG. 1.

The article includes a second piece 2 which, as can be seen from FIGS. 1 and 4, consists of an outer layer 3, an inner layer 4 and an absorbent element 5 arranged between these. In the embodiment in plane form shown in FIG. 1, this element is essentially triangular. The material selected for the absorption element can be chosen from among materials or material combinations well-known to the person skilled in the art. For example, the absorbent element can consist of cellulose fluff pulp with superabsorbent materials in powder or fiber form added in. The absorbent element can also consist of a foam material with or without superabsorbent material.

The outer layer 3 may suitably be liquid-impermeable and breathable. The breathable and liquid-impermeable layer 3 may have a so-called MTVR-value in the order of magnitude of 200-10000 g/m²/24 h. The term MTVR stands for "Moisture Vapor Transmission Rate", i.e., the amount of vapor which can pass per unit area during a certain period of time. Said breathable portion suitably has an MTVR-value in the order of magnitude of 500-5000 g/m²/24 h, and most preferably in the order of magnitude of 1000-3000 g/m²/24 h.

Measurement of breathability has been performed with the method ASTM E96 and the measurement equipment Lyssy has been used.

A problem with absorbent articles of pants-like shape is namely that conventional articles of this kind tightly enclose the area around the genitals of the wearer, whereby this area, when body fluids are excreted, becomes locally saturated with moisture and vapor, which has an adverse effect on the skin of the wearer. In some cases disturbing skin irritation can occur. Furthermore, also minor chafing of the article against the skin of the wearer, in combination with a moist environment and during lengthy usage of the article, can give rise to sores on older people with flesh that heals poorly.

It is not required that the elastic first piece is liquid-impermeable. The elastic first piece 1 should have good breathability Breathable and vapor-permeable but liquid-impermeable materials for use in absorbent articles, such as diapers, incontinence products or sanitary towels, are previously known. Breathable materials can consist of perforated plastic films, as described in U.S. Pat. No. 5,628,737, or of micro-porous plastic films, as described in, for example, EP-A-0238200. Another example of breathable materials are so-called non-woven materials which are air-permeable and vapor-permeable and which, if required, have been treated with means to improve the liquid-impermeability, as is described in EP-A-0196654. In absorbent articles of pants-like shape, with a fit which tightly encloses around the wearer, the need for air-permeability and vapor-permeability is beneficial.

The liquid-impermeable and breathable layer 3 can, for example, consist of a perforated polyethylene film, where the size of the holes has been chosen so that air and vapor may pass, but not liquid drops. If an absorbent article with a more textile-like appearance is desired, a liquid-impermeable film in combination with an outer fiber layer is suitable.

The inner layer 4 can be made from a liquid-permeable non-woven.

Figure 2:
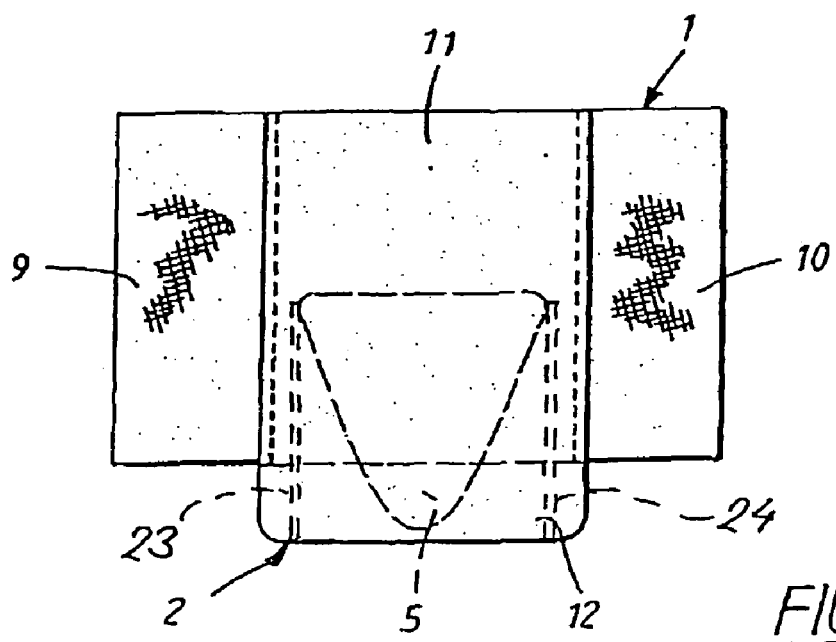
FIG. 2 shows schematically in plane form an assembled article according to the first embodiment.
Figure 3:
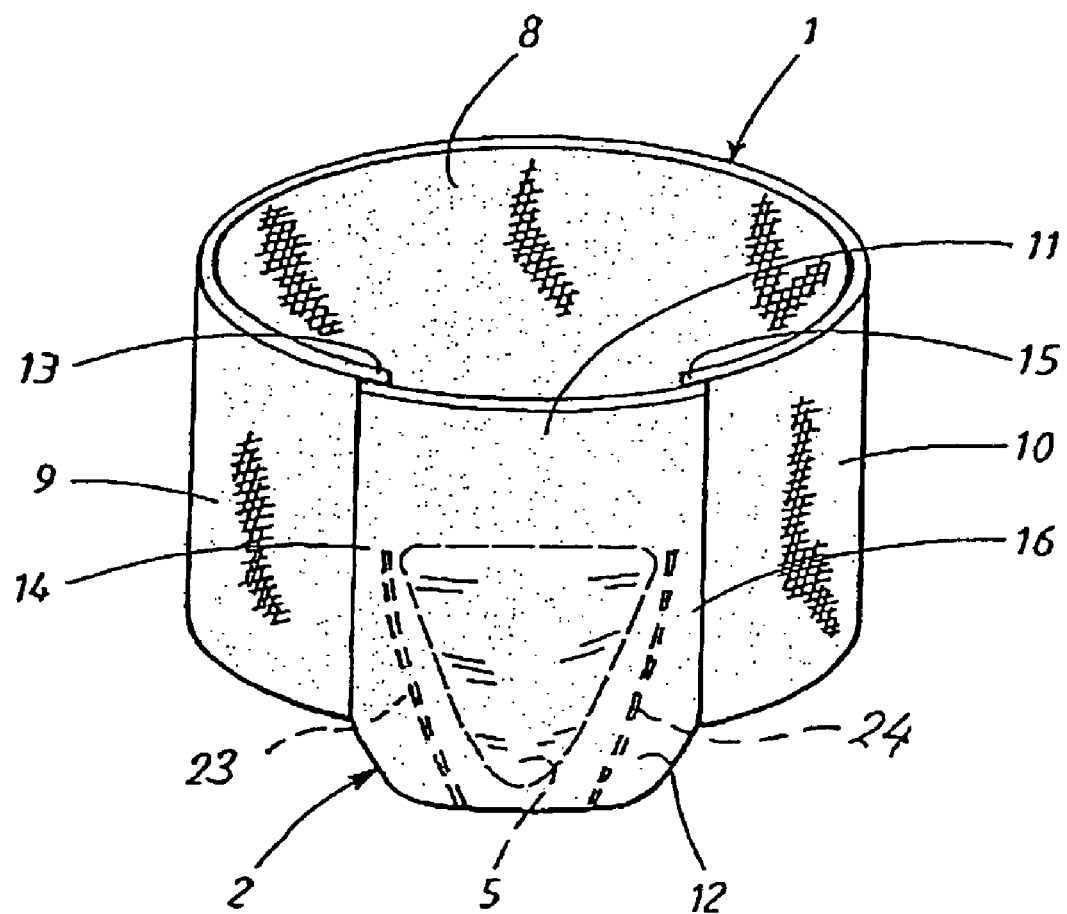
FIG. 3 shows the article according to FIG. 2 in perspective.

The second piece 2 is elongate and is arranged with its longitudinal direction at right angles in relation to the longitudinal direction of the first piece 1. The second piece 2 is connected by one end portion 6 to one longitudinal edge portion 7 of the first piece 1, centrally thereon. The connection can be made by means of, for example, adhesive, thermal bonding or ultrasonic bonding. Elastic members 23,24 are arranged along the edge portions of the second piece, which elastic members, in the shown embodiment, are made from elastic bands, extending from the first piece 1, over the crotch portion and over the entire extent of the absorbent element 5. During use of the article, the elastic members are intended to serve as leg elastics and to lie in sealing contact with the legs of the wearer along the crotch portion of the wearer, as is shown in FIGS. 2 and 3. The elastic members 23,24 may be arranged in prestressed condition on the second piece 02. Alternatively, the elastic members may be made of a material which is arranged in an unstressed, untensioned condition, and which shrinks and becomes elastic only when heated. Such elastic members are well known to the person skilled in the art and are for this reason not further described. Elastic members which become effective only on thermal treatment are suitably subjected to required thermal treatment only when the absorbent articles are arranged in packages, whereby processing and packaging are simplified compared to elastic members which are arranged on the second piece 102 in prestressed condition.

In FIG. 1, the arrows A and B illustrate how the first and second pieces are folded to form the absorbent article of pants-like shape shown in FIGS. 2 and 3. The elastic piece 1 is folded in according to the arrows A shown to form the rear portion 8 and side portions 9, 10 of the article, while the second piece is folded upwards according to the arrows B to form the front portion 11 and crotch portion 12 of the article.

As can be seen most clearly from FIG. 3, one end portion 13 of the first piece is arranged so as to be overlapped a little by a first side edge portion 14 of the second piece, and the other end portion 15 of the first piece is in a corresponding manner arranged so as to be overlapped a little by a second side edge portion 16 of the second piece. These overlapping portions are interconnected by means of, for example, adhesive, thermal bonding or ultrasonic bonding. Alternatively the front portion and the crotch portion can be arranged detachably along said overlapping portions 13, 14 and 15, 16. Such a detachable connection can be made by means of, for example, hook means (not shown), as a result of which the pants-like article can be opened and subsequently reclosed with the same fit and tightness.

In FIG. 4, the thickness of the second piece has been exaggerated for the sake of clarity. The figure shows an outer layer 3 consisting of a laminate of a plastic film 17 and a non-woven layer 18 arranged outside. The inner layer 4 can consist of a liquid-permeable non-woven of a type well-known to the person skilled in the art.

Figure 5:
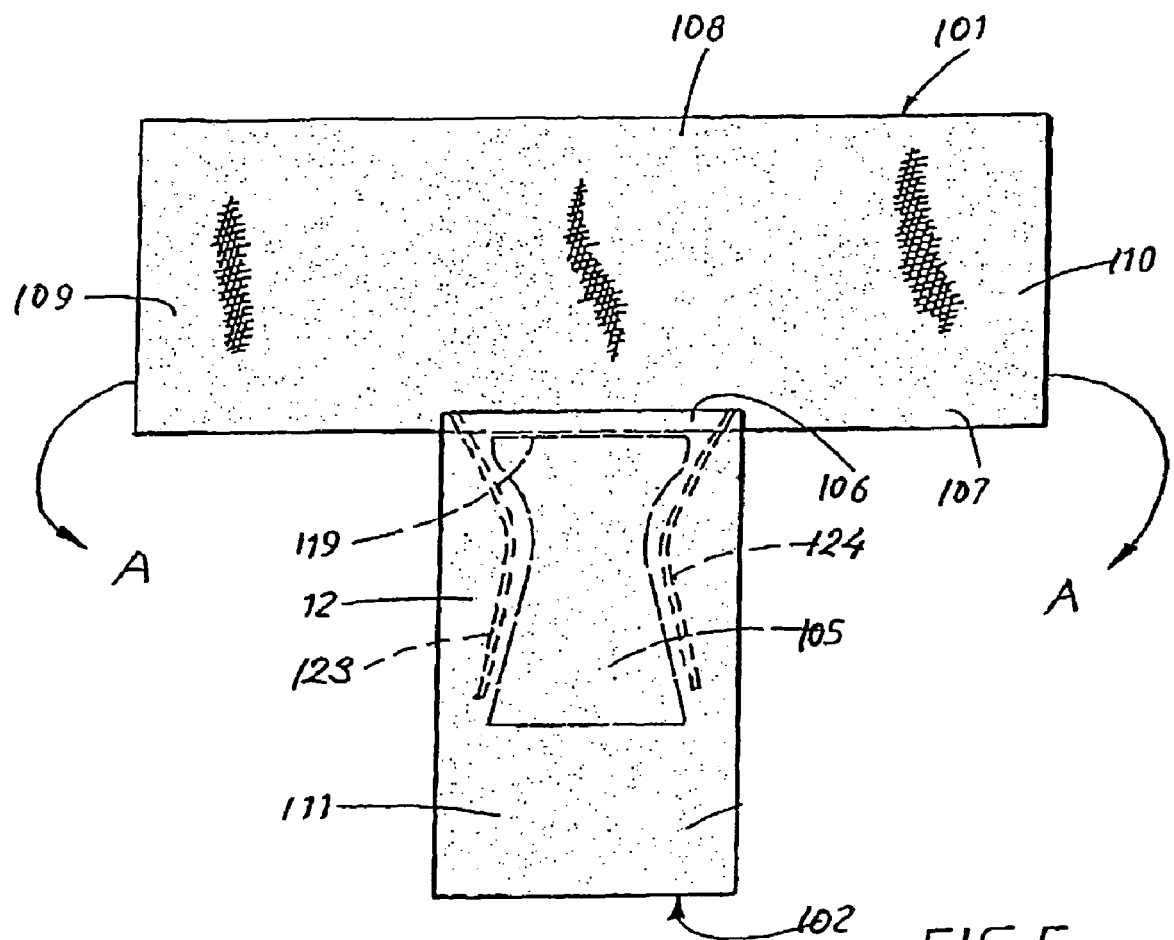
FIG. 5 shows schematically a phase of the construction of an absorbent article according to a second embodiment.
Figure 6:
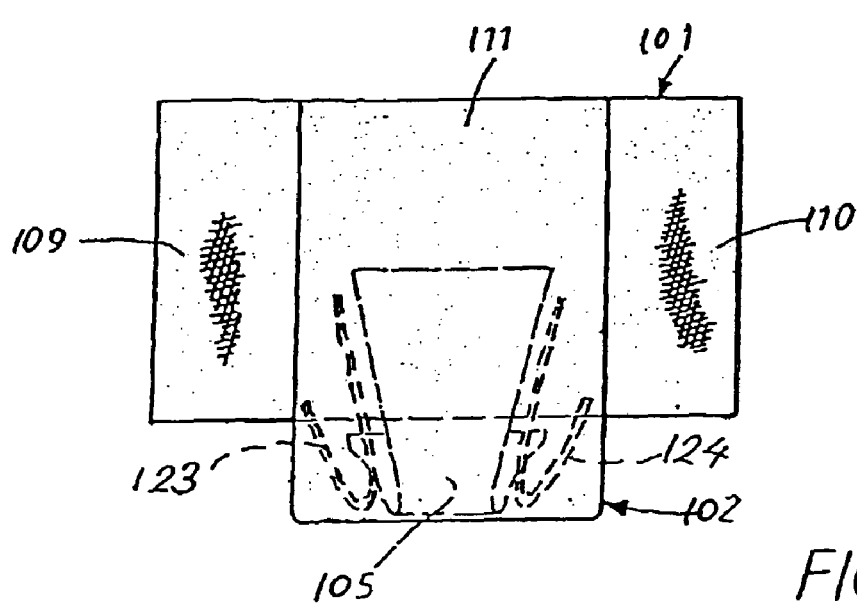
FIG. 6 shows in plane form an assembled article according to the second embodiment.

In the embodiment shown in FIGS. 5 and 6, those parts corresponding to the same parts in the embodiment according to FIGS. 1-4 have been provided with the same reference numbers except increased by 100. The only difference between the embodiment according to FIGS. 5 and 6 and the embodiment described above is the shape and extent of the absorbent element 105, and the extent of the elastic members 123,124. In this second embodiment, the absorbent element 105 is hourglass-shaped in plane form, as can be seen most clearly from FIG. 5, the narrower portion being intended to be arranged in the crotch of the wearer during use of the article. The upper end edge 119 of the absorbent element 105 is located directly adjacent to the lower edge portion 107 of the first elastic piece, which means that the absorbent element according to this second embodiment extends over the entire crotch area and a little way up over the front portion 111, as can be seen from FIG. 6. The elastic members 123,124 are arcuately arranged along the side edges of the absorbent element 105 and extend, as is evident from FIG. 5, from the upper elastic first piece 101 and down over the crotch portion of the article. As is evident from FIG. 5, the end portions of the elastic members 123,124 bridge that end portion 106 of the second piece which overlaps the first elastic piece 101. Thus, the elastic members are operatively connected, in the rear portion 108 of the article, with the first elastic piece 101. The opposite end of each elastic member 123,124 does not extend all the way to the side edges of the second piece 102, but are arranged so that the elastic members in the state of use of the article, which is shown in FIG. 6, do not reach all the way to the side portions 109,110 of the first elastic piece. The relationship is the same in the embodiments according to FIGS. 2 and 3.

Preferably, the elastic piece 101 and the elastic members have an elastic characteristic which allows an extension of up to the order of magnitude of twice the length with constant extension force. An absorbent article of a certain size can thereby be used on wearers of different sizes without the pressure from the elastic being varied, which in its turn leads to a very limited assortment of different sizes of the absorbent article being required in order to cover the need of sizes for wearers of different sizes.

In the embodiment shown in FIGS. 5 and 6, the second piece 102 has been shaped rectangular. The second piece 102 may, of course, be provided with leg cut-outs which follow the curved elastic members and the curved edge portions of the hourglass-shaped absorbent element 205.

Figure 7:
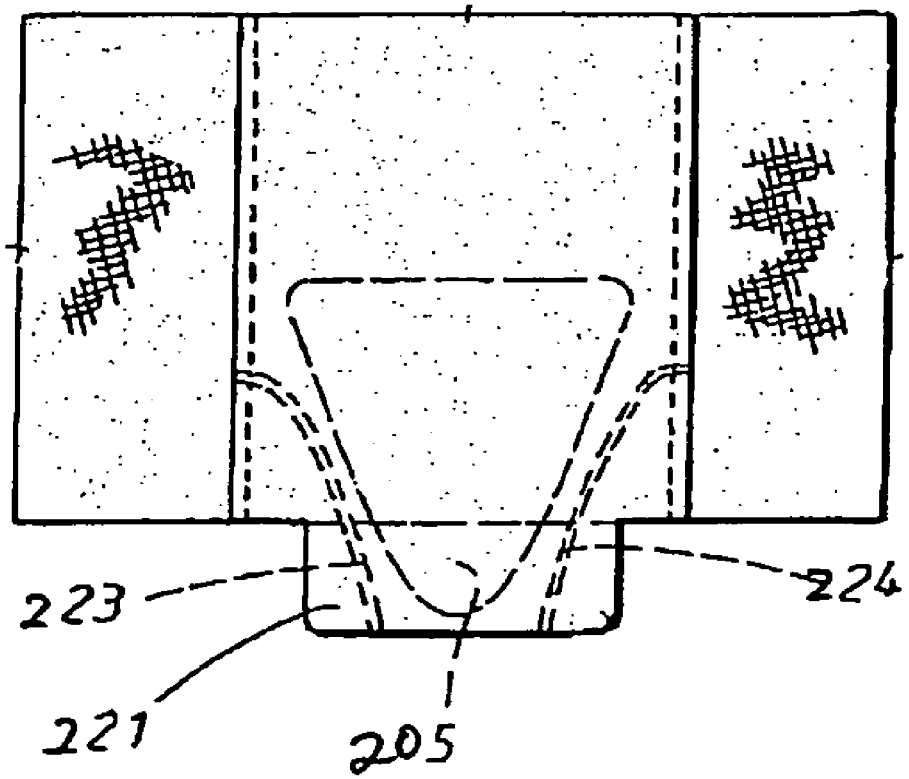
FIG. 7 shows in plane form an assembled article according to a third embodiment.

FIG. 7 shows a third embodiment which is slightly modified in relation to the first embodiment. The difference is that the elastic members 223,224 have another extent and that a part piece 221 of the second piece is made narrower than the remainder of the second piece, in which way a pants-like article with a narrower crotch portion is obtained, as can be seen from FIG. 7. In this embodiment the elastic members 223,224 extend to the edge sides of the second piece and into each joint between the pieces, as can be seen from FIG. 7.

Figure 8:
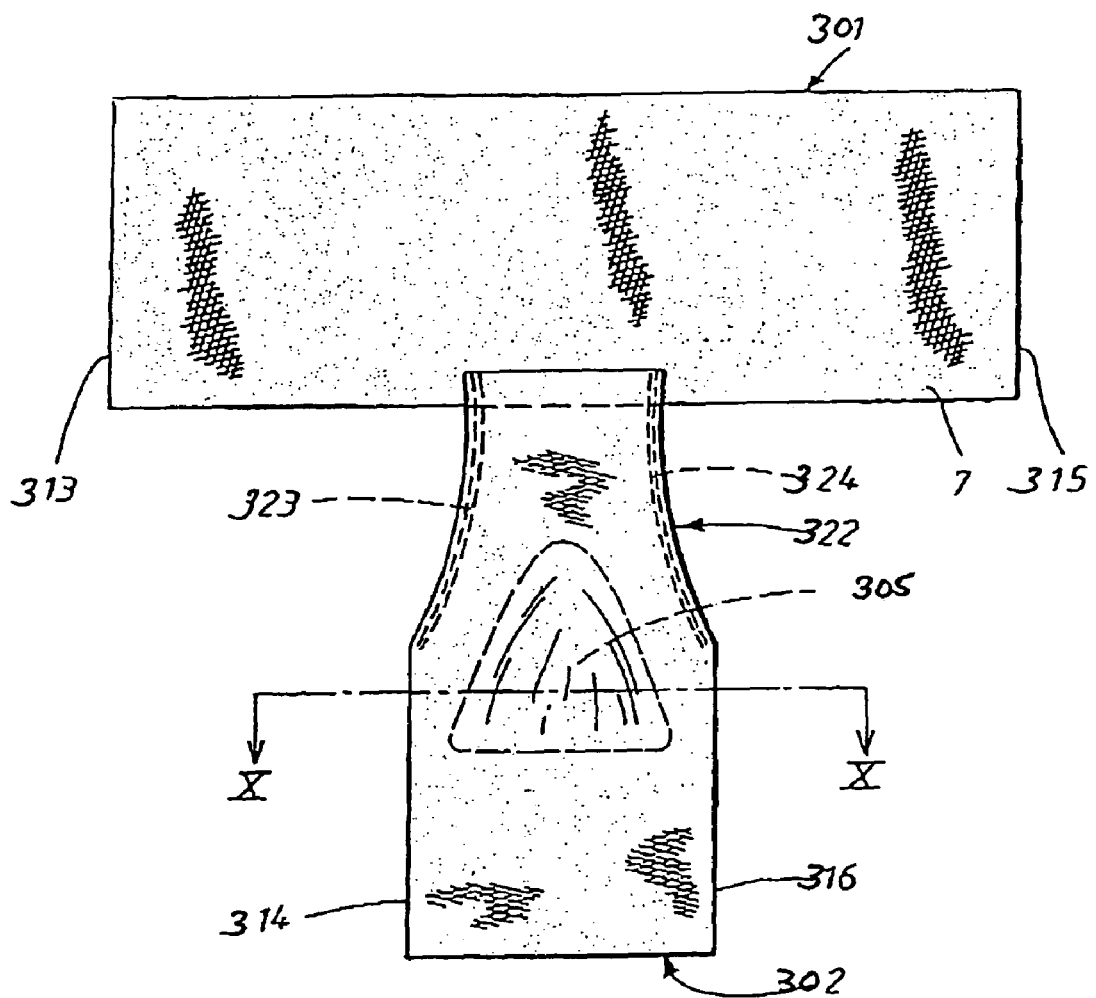
FIG. 8 shows in plane view an assembled article according to a fourth embodiment of the invention.

In the embodiment shown in FIG. 8, the details corresponding to similar details in the other embodiments have been provided with the same reference numbers, except increased by 300. The second piece 302 has a concave portion 322 which extends from the first piece 301 towards the side edge portions 314,316. These are, as in the above described embodiments, intended to be connected with the end portions 313 and 315 on the first piece 301.

The first piece 301 is formed of an elastic material and is intended during use of the article to achieve an elastic tightening around the waist of the wearer, which tightening keeps the article in place and gives it a good fit. In the embodiment shown in FIG. 8, the elastic members 323,324 are arranged along both sides of the concave portion 322 for the forming of leg elastic, which during use of the article is intended to be in sealing contact with the legs of the wearer. In the shown embodiment, the elastic members 323,324 extend from the elastic first piece 301 to the side edge portions 314,316. The completed, assembled, pants-like article will thereby be elastically tight-fitting around both of the legs of the wearer. In this manner a good fit is obtained. If the elastic piece 301 and the elastic members 323,324 are formed so that they are elastically stretchable a longer distance, without the tension in the elastic piece 301 and in the elastic members 323,324 being increased to any considerable extent, the article can, as described above, without any annoying chafing, be used by wearers of different sizes. In such a design, the number of requisite sizes can be kept down, which leads to savings and rational manufacturing compared to if there is a need for a larger assortment of sizes.

Figure 9:
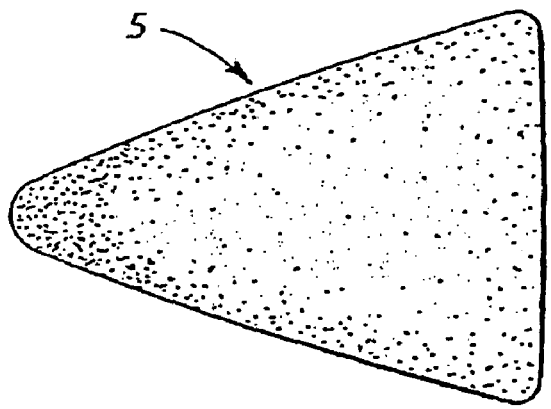
FIG. 9 shows schematically the distribution of superabsorbent material in one embodiment of an absorbent element belonging to the article.

FIG. 9 schematically shows the absorbent element 5, 105, 205, 305 usable in the embodiments 5, 105, 205, 305 of FIGS. 1-4 and 7-8. In order to avoid giving rise to annoying chafing in the crotch of the wearer, the absorbent element has been designed as narrowing in that direction which during use of the article is directed rearwards. A complication with this narrowing design is that the absorbent element is narrowest in that portion which during use of the article is situated substantially in front of the genitals of the wearer, in which portion the demand for absorption capacity is greatest. To avoid the risk of leakage in the narrower portion of the absorbent element to the most practicable degree, the superabsorbent material, according to a suitable embodiment where the superabsorbent material is part of the absorbent element in the form of particles or fibers, has been arranged with an increasing concentration in said narrowing direction. This has been illustrated in FIG. 9 with the number of shown dots in correspondence with a gradient of the number of superabsorbent particles per unit volume of the absorbent element 5, 105, 205, 305 in said direction.

Figure 10:
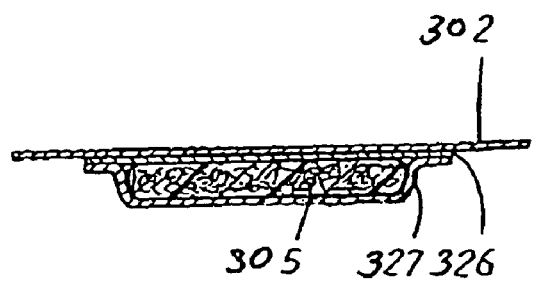
FIG. 10 shows a section along the line X-X in FIG. 8.

In FIG. 4 an embodiment is shown where the liquid-impermeable but breathable outer layer 3 consists of a layer of the second piece. According to one embodiment, the liquid-impermeable outer layer is arranged only over the absorbent element, and forms an outer layer of said element. In FIG. 10 a cross section along the line X-X in FIG. 8 is shown, in order to illustrate this. The absorbent element is here enclosed between a liquid-permeable layer 326, for example, of non-woven, and of a liquid-impermeable and at the same time breathable layer 327, for example, of a perforated plastic film. The two layers 326,327 extend beyond the absorbent element 305 and a distance around it and are there interconnected. The unit formed by the absorbent element 305 and the two layers 326 and 327 is attached to the second piece 302 of the absorbent article, wherein the liquid-permeable layer 326 has been connected to the second piece 302, as is shown in FIG. 10.

The absorption unit shown in FIG. 10, consisting of the absorbent element 305 and the layers 326 and 327, may be replaced with an absorbent foam material in one piece, which foam material is provided with an integral liquid-impermeable and at the same time air-permeable layer.

When the expression liquid-impermeable and breathable has been used in the above text, it also implies that the material in question also is vapor-permeable, but that it does not allow passage of liquid drops.

The liquid-impermeable outer layer 3 can, within the scope of the invention, be made of an air-impermeable material.

In the above illustrative embodiments, as is evident from FIG. 3, the side edge portions 14,16 of the second piece have been arranged on the outside of the end edge portions 13,15 of the first piece. It is, of course, possible to do the reverse, i.e., with the end edge portions 13,15 of the first piece farthest out. These two alternatives are to be preferred, even though it is within the scope of the invention to obtain said connection by means of attaching the inside of each of the end edge portions of the first piece to the inside of each side edge portion of the second piece, or by means of connecting corresponding edge portions outside to outside.

The article according to the invention has turned out to be especially suitable as incontinence shields for men. Other applications, such as menstrual shields or incontinence shields for women, are also conceivable.

In the above described illustrative embodiments, the highest absorption capacity per unit area for the narrowest area has been achieved by means of varying the content of superabsorbent material. Another method of achieving higher absorption capacity in the narrowest area is to form the absorbent element with a higher basis weight in this area. This can, for example, be carried out on an absorbent element formed from a fluff pulp of cellulose. Thus, the absorption capacity for an absorbent element of a fluff pulp may also be controlled by varying the density and/or the thickness in different portions.

The absorbent element can, of course within the scope of the invention, be formed from other materials, for example absorbent foam materials.

The invention is not limited to the illustrative embodiments described above, but a number of modifications are possible within the scope of the patent claims below.

The invention claimed is:

1. A method of manufacturing an absorbent article, comprising:
   providing an elastically stretchable first piece having first and second lateral edges and first and second ends, wherein the first and second ends are shorter than the first and second lateral edges;

securing a first end of a second piece of material to a middle portion of the second lateral edge of the first piece so that the first piece extends substantially perpendicular to the second piece, wherein the second piece has first and second longitudinal edges that are substantially perpendicular to the first end and the first end is shorter than the first and second longitudinal edges, and wherein the second piece includes an absorbent element;

securing the first end of the first piece to the first longitudinal edge of the second piece and securing the second end of the first piece to the second longitudinal edge of the second piece; and providing elastic members along at least a portion of the first longitudinal edge and along at least a portion of the second longitudinal edge of the second piece adjacent the absorbent element to contract said portions of the second piece.

2. The method of claim 1, wherein the first piece is substantially rectangular.

3. The method of claim 2, wherein the second piece is substantially rectangular.

4. The method of claim 1, wherein the second piece is substantially rectangular.

5. The method of claim 1, wherein a portion of the absorbent element is between the first and second edges of the first piece and a portion of the absorbent element is not between the first and second edges of the first piece.

6. The method of claim 1, wherein the absorbent element includes superabsorbent materials.

7. The method of claim 1, wherein the absorbent element is hourglass shaped.

8. The method of claim 1, wherein one portion of the second piece is narrower than a remainder of the second portion.

9. A method of manufacturing an absorbent article, comprising:

providing an elastically stretchable first piece having first and second lateral edges and first and second ends, wherein the first and second ends are shorter than the first and second lateral edges;

securing a first end of a second piece of material to a middle portion of the second lateral edge of the first piece so that the first piece extends substantially perpendicular to the second piece, wherein the second piece has first and second longitudinal edges that are substantially perpendicular to the first end and the first end is shorter than the first and second longitudinal edges, and wherein the second piece includes an absorbent element;

securing the first end of the first piece to the first longitudinal edge of the second piece and securing the second end of the first piece to the second longitudinal edge of the second piece; and providing elastic members along at least a portion of the first longitudinal edge and along at least a portion of the second longitudinal edge of the second piece adjacent the absorbent element to contract said portions of the second piece, wherein the first end of the absorbent element is closer to the first edge of the second piece that the second end of the absorbent element.

10. A method of manufacturing an absorbent article of pants shape, the absorbent article comprising an elastic waist portion, an absorbent element, which has a length and a width and which covers genitals of a wearer when the article is worn, and a liquid-impermeable outer layer which encloses the absorbent element on at least a side thereof which faces away from the wearer of the article, the method comprising:

forming said elastic waist portion from an elastic first piece which is elongate in an extended state and partly surrounds the trunk of the wearer and forms a rear portion and side portions of the pants article when the article is worn, forming a front portion of the article and a crotch portion from a second piece, said second piece is elongate with two opposite end edges and two opposite longitudinal edges, a width of the second piece is, at least in the crotch portion, smaller than a length of the first piece, the second piece is arranged with its longitudinal direction at right angles in relation to the lateral direction of the first piece, connecting a first end portion of the second piece to one lateral edge portion of the first piece, centrally thereon, connecting one end portion of the first piece to a first longitudinal edge portion of the second piece, and connecting another end portion of the first piece in a corresponding manner to a second longitudinal edge portion of the second piece, and elastic members are arranged in the crotch portion on each side of the absorbent element.

11. The method according to claim 10, wherein the absorbent element in its entirety is arranged on the second piece forming part of the article before said piece is connected to said first piece.

* * * * *